United States Patent [19]

Rao

[11] Patent Number: 4,772,729
[45] Date of Patent: Sep. 20, 1988

[54] HYDROGENATION OF CITRIC ACID AND SUBSTITUTED CITRIC ACIDS TO 3-SUBSTITUTED TETRAHYDROFURAN, 3- AND 4-SUBSTITUTED BUTYROLACTONES AND MIXTURES THEREOF

[75] Inventor: Velliyur N. M. Rao, Wilmington, Del.

[73] Assignee: E. I. Du Pont de Nemours and Company, Wilmington, Del.

[21] Appl. No.: 6,237

[22] Filed: Jan. 23, 1987

[51] Int. Cl.$^4$ .................. C07D 307/32; C07D 307/08
[52] U.S. Cl. ..................................... 549/326; 549/508
[58] Field of Search ........................ 549/325, 326, 508

[56] References Cited

U.S. PATENT DOCUMENTS

| 4,096,156 | 6/1978 | Freudenberger et al. | 549/326 |
| 4,105,674 | 8/1978 | De Thomas et al. | 549/326 |
| 4,550,185 | 10/1985 | Mabry et al. | 549/508 |
| 4,609,636 | 9/1986 | Mabry et al. | 502/183 |

FOREIGN PATENT DOCUMENTS

| 2133768 | 1/1972 | Fed. Rep. of Germany | 549/325 |
| 1149784 | 4/1969 | United Kingdom | 549/325 |

OTHER PUBLICATIONS

Abstract of JA-7300823-R (Jan. 1973).
Abstract of J6 1115-079-A (Jun. 1986).

*Primary Examiner*—Norma S. Milestone

[57] ABSTRACT

A process is disclosed for preparing 3-substituted tetrahydrofuran, 3- and 4-substituted butyrolactones and mixtures thereof comprising hydrogenating a hydrogenatable precursor in the presence of an aqueous reaction medium and a catalyst comprising palladium and rhenium and at least one support selected from the group consisting of titanium oxide, zirconium oxide, and carbon.

9 Claims, No Drawings

4,772,729

HYDROGENATION OF CITRIC ACID AND SUBSTITUTED CITRIC ACIDS TO 3-SUBSTITUTED TETRAHYDROFURAN, 3- AND 4-SUBSTITUTED BUTYROLACTONES AND MIXTURES THEREOF

FIELD OF THE INVENTION

The present invention relates to a process for making 3-substituted tetrahydrofuran, 3- and 4-substituted butyrolactones and mixtures thereof by hydrogenation of citric acid and substituted citric acids.

BACKGROUND OF THE INVENTION

Butyrolactone is a known compound which is employed in the synthesis of pyrrolidone, glutaric acid, and many other compounds. 3-Substituted tetrahydrofuran is employed as monomer in copolymers. Improved processes for preparing butyrolactone and 3-substituted tetrahydrofuran are of interest to the chemical industry.

The following references disclose known processes for making butyrolactone. U.S. Pat. No. 4,096,156 discloses a process for the preparation of gamma-butyrolactone by catalytic hydrogenation of maleic acid, maleic acid anhydride, succinic acid, succinic acid anhydride, or fumaric acid, or of a mixture of two or more of these compounds. The catalyst contains a mixture of an element of the VIII$^{th}$ subgroup of the periodic system of elements or of one of its compounds with an element of group IB of the periodic system of elements or of one of its compounds.

U.S. Pat. No. 4,105,674 discloses a process for producing gamma-butyrolactone by hydrogenating a feed compound selected from the group consisting of maleic acid, succinic acid, maleic anhydride, succinic anhydride, and mixtures of any of the foregoing in the vapor phase. The reaction is conducted in the presence of a Cu-Pd or Cu-Pt catalyst.

SUMMARY OF THE INVENTION

The present invention provides a process for preparing 3-substituted tetrahydrofuran, 3- and 4-substituted butyrolactones and mixtures thereof comprising hydrogenating a hydrogenatable precursor in the presence of an aqueous reaction medium and a catalyst comprising palladium and rhenium and at least one support selected from the group consisting of titanium oxide, zirconium oxide, and carbon.

DETAILED DESCRIPTION OF THE INVENTION

The invention a process for making 3-substituted tetrahydrofuran, 3- and 4-substituted butyrolactones and mixtures thereof by hydrogenating a hydrogenatable precursor such as citric acid, substituted citric acid, or mixtures thereof. A partial list of suitable substitutions for the hydrogenatable precursor includes H, $CH_3$, $C_2H_5$ and $C_3H_7$. Preferably, the hydrogenatable precursor is citric acid. The processes of the invention are characterized in that they can be oriented, as desired, toward high ratios of 3-substituted tetrahydrofurans to 3- and 4-substituted butyrolactones or vice versa.

The catalyst of this invention comprises palladium and rhenium and at least one support selected from the group consisting of titanium oxide, zirconium oxide, and carbon. Preferably, the support is titanium oxide or carbon, and most preferably, the catalyst comprises from about 1 to about 19 weight percent palladium and from about 4 to about 76 weight percent rhenium. The catalyst provides high conversion of the precursor, high selectivity to and yield of product, and the advantage of being able to control the product ratio of 3-substituted tetrahydrofuran/3- and 4-substituted butyrolactone by varying the support. It has been found that carbon supported catalysts favor the production of 3-substituted tetrahydrofurans and that titanium oxide and zirconium oxide supported catalysts favor production of 3- and 4-substituted butyrolactones.

Preferably, the process is conducted at a temperature of from about 100° C. to about 300° C., and most preferably from about 150° C. to about 250° C. Preferably, the process is conducted at a pressure of from about 3.5 MPa (500 psig) to about 27.6 MPa (4000 psig), and most preferably from about 3.5 MPa (500 psig) to about 17.3 MPa (2500 psig).

The process is conducted in the presence of an aqueous reaction medium which can be water or an aqueous solution containing water soluble substances such as methanol, ethanol, tetrahydrofuran or 1,4-dioxane. Preferably, the aqueous reaction medium is water. The concentration of precursor is not critical. The precursor can be employed in dilute solutions to near the maximum solubility level, typically from about 1 to about 50 weight percent.

The liquid phase hydrogenation of the invention can be run using conventional apparatus and techniques in a stirred-tank reactor or in a fixed-bed reactor. Hydrogen is fed continuously, generally in considerable stoichiometric excess with no inert diluent gases. Unreacted hydrogen can be returned to the reactor as a recycle stream. The reaction can be run in the batch or continuous mode.

The invention is further described in the following examples wherein all parts and percentages are by weight and degrees are Celsius. Catalysts used in the Examples and Comparative Experiments were prepared according to the following general precedure.

Catalyst Preparation

The catalysts were prepared by adding 20 g of support to a solution containing 0.33 g of $PdCl_2$, 3 mL of concentrated hydrochloric acid and 15 mL of distilled water. The resultant slurry was stirred for three hours at ambient temperature and dried at 110° for 18 hours. The resulting supported catalyst was then heated in a furnace for one hour at 150° in an atmosphere of helium (flow rate 100 mL/min), followed by heating at 150° for one hour and 300° for three hours in an atmosphere of helium (flow rate 100 mL/min) and hydrogen (flow rate 100 mL/min). While still maintaining the hydrogen helium atmosphere, the catalyst was cooled to ambient temperature and passivated at ambient temperature with an atmosphere of 1.8% oxygen in nitrogen for 18 hours.

The resulting reduced catalyst was added to a solution containing the desired amount of ammonium perrhenate and 6 mL of distilled water. The resultant slurry was treated as described above.

The catalyst so prepared were granulated to 16 to 19 mesh (U.S. Standard Sieve Units) and charged into the reactor employed in the Examples. Prior to start of the liquid feed the granulated catalysts were reduced in the reactor for about two hours each at 100°, 150°, and 200° in a stream of hydrogen.

EXAMPLE 1

Hydrogenation of Citric Acid to 3-Methyltetrahydrofuran

A fixed bed reactor having a volume of 6 mL was charged with 1.73 g of 1% palladium and 4% rhenium on carbon catalyst. A 5% solution of citric acid monohydrate in water was passed through the reactor at a flow rate of 11.2 mL/minute along with hydrogen at a flow rate of 50 mL/minute. Optimum performance was obtained at an operating pressure of 6.9 MPa (1000 psig) and a temperature of 250°. Contact time was approximately 30 minutes based on the empty reactor volume. The citric acid conversion was greater than 99%. The product leaving the reactor was analysed by gas chromatography. The selectivity to 3-methyl tetrahydrofuran was 70.4%.

EXAMPLE 2

Hydrogenation of Citric Acid to 3 and 4-Methylbutyrolactones

A Hastelloy reactor having a volume of 6 mL was charged with 1.73 g of 1% palladium and 4% rhenium on titanium oxide catalyst. A 5% solution of citric acid monohydrate in 98% water and 2% dioxane was passed through the reactor at a flow rate of 12 mL/ hour along with hydrogen at a flow rate of 100 mL/minute. Near complete conversion of citric acid was achieved at an operating pressure of 6.9 MPa (1000 psig), a temperature of 250° and a contact time of about 30 minutes, based on an empty reactor volume. The product leaving the reactor was analysed by gas chromatography. The analysis showed 55.1% of 3 & 4-methylbutyrolactones and 8.5% of 3-methyltetrahydrofuran.

What is claimed is:

1. A process for preparing 3-substituted tetrahydrofuran, 3- and 4-substituted butyrolactones and mixtures thereof comprising contacting a hydrogenatable precursor selected from the group consisting of citric acid and substituted citric acid with a catalyst comprising palladium and rhenium and at least one support selected from the group consisting of titanium oxide, zirconium oxide, and carbon in the presence of an aqueous reaction medium and hydrogen.

2. A process according to claim 1, wherein the hydrogenatable precursor is citric acid.

3. A process according to claim 1, wherein the support is titanium oxide or carbon.

4. A process according to claim 3, wherein the catalyst comprises from about 1 to about 19 weight percent palladium and from about 4 to about 76 weight percent rhenium.

5. A process according to claim 4, wherein the process is conducted at a temperature of from about 100° C. to about 300° C.

6. A process according to claim 5, wherein the process is conducted at a temperature of from about 150° C. to about 250° C.

7. A process according to claim 6, wherein the process is conducted at a pressure of from about 3.5 MPa to about 27.6 MPa.

8. A process according to claim 7, wherein the process is conducted at a pressure of from about 3.5 MPa to about 17.3 MPa.

9. A process according to claim 8, wherein the aqueous reaction medium is water.

* * * * *